United States Patent [19]

Baraff

[11] Patent Number: 5,326,349
[45] Date of Patent: Jul. 5, 1994

[54] ARTIFICIAL LARYNX

[76] Inventor: David R. Baraff, 630 Llewelyn Rd., Berwyn, Pa. 19312

[21] Appl. No.: 910,217

[22] Filed: Jul. 9, 1992

[51] Int. Cl.⁵ .................... A61F 2/20; A61C 13/00
[52] U.S. Cl. ........................ 623/9; 381/70; 433/167
[58] Field of Search .............. 623/9; 381/70; 433/32, 433/167, 201.1

[56] References Cited

U.S. PATENT DOCUMENTS

| | | |
|---|---|---|
| 1,901,433 | 5/1931 | Burchett . |
| 2,041,487 | 5/1936 | Riesz . |
| 2,056,295 | 10/1936 | Riesz . |
| 2,058,212 | 10/1936 | Burchett . |
| 2,202,467 | 5/1940 | Riesz . |
| 2,273,077 | 2/1942 | Wright . |
| 2,862,209 | 12/1958 | Cooper . |
| 2,868,876 | 1/1959 | Ticchioni . |
| 3,066,186 | 11/1962 | Trammell . |
| 3,072,745 | 1/1963 | Barney . |
| 3,291,912 | 12/1966 | Flanagan . |
| 3,508,000 | 4/1970 | Snyder . |
| 3,524,932 | 8/1970 | Stucki . |
| 3,766,318 | 10/1973 | Webb . |
| 3,914,550 | 10/1975 | Cardwell, Jr. ............ 381/70 |
| 4,028,492 | 6/1977 | Sickel . |
| 4,039,756 | 8/1977 | Burtschi ................... 381/70 |
| 4,292,472 | 9/1981 | Lennox . |
| 4,338,488 | 7/1982 | Lennox ................... 623/9 X |
| 4,473,905 | 9/1984 | Katz et al. ............. 623/9 X |
| 4,489,440 | 12/1984 | Chaoui ..................... 381/70 |
| 4,502,151 | 2/1985 | Castle et al. . |
| 4,539,698 | 9/1985 | Katz et al. ............. 623/9 X |
| 4,547,894 | 10/1985 | Benson et al. ............ 381/70 |
| 4,550,427 | 10/1985 | Katz et al. . |
| 4,571,739 | 2/1986 | Resnick .................... 381/70 |
| 4,672,673 | 6/1987 | Katz et al. ............. 623/9 X |
| 4,706,292 | 11/1987 | Torgeson ............... 623/9 X |
| 4,726,066 | 2/1988 | Bloomfield, III . |
| 4,993,071 | 2/1991 | Griebel .................... 381/70 |

FOREIGN PATENT DOCUMENTS

| | | |
|---|---|---|
| 0058077 | 8/1982 | European Pat. Off. ........... 623/9 |
| 0108595 | 5/1984 | European Pat. Off. ........... 623/9 |
| 2818853 | 11/1978 | Fed. Rep. of Germany ....... 623/9 |
| 1592872 | 7/1981 | United Kingdom ............ 381/70 |
| 2179522 | 3/1987 | United Kingdom ............. 623/9 |

OTHER PUBLICATIONS

Debreceni, A. E., et al. "An Implantable Electromagnetic Sound Source for Speech Production", vol. XXIII, Trans. Am. Soc. Artif. Intern. Organs, 1977 pp. 22–26.

Dennis H. Klatt & L. C. Klatt "Analysis, synthesis, and perception of voice equality variations among female and male talkers" Oct. 1989.

Kenneth J. Stern "A Self Contained Intra-Oral Artificial Larynx" Senior Design Project B.E. 495.

Kenneth J. Stern "A Self-Contained Intra-Oral Artificial Larynx" Progress Report Dec. 1978.

Kenneth Stern "Senior Design Project"–A Self-Contained Intra-Oral Artificial Larynx.

*Primary Examiner*—David J. Isabella
*Assistant Examiner*—Elizabeth M. Burke
*Attorney, Agent, or Firm*—O'Keefe & Wilkinson

[57] ABSTRACT

An artificial larynx consists of (1) a first unit mounted in the mouth comprising a dental prosthesis, including a loud speaker, a power amplifier, a self-contained power source, plus a radio frequency receiver, and (2) a second unit held in the hand equipped with an input control device, self-contained power source, electronic circuitry and transmitter allowing the user to alter the frequency and volume produced by the unit in the mouth. The construction and components of the unit allows laryngectomees to speak with both a natural sound and a high degree of intelligibility. The unit preferably includes a system architecture including operational software which implements predetermined control of a fundamental repetition rate of voice pulses provided by the unit, to control the tonal quality of the sound, to include aspiration noise in the sound, to include pseudorandom variation of the fundamental repetition rate of the tonal pulse, includes diplophonic structure in such pulse and is able to simulate whispering.

28 Claims, 9 Drawing Sheets

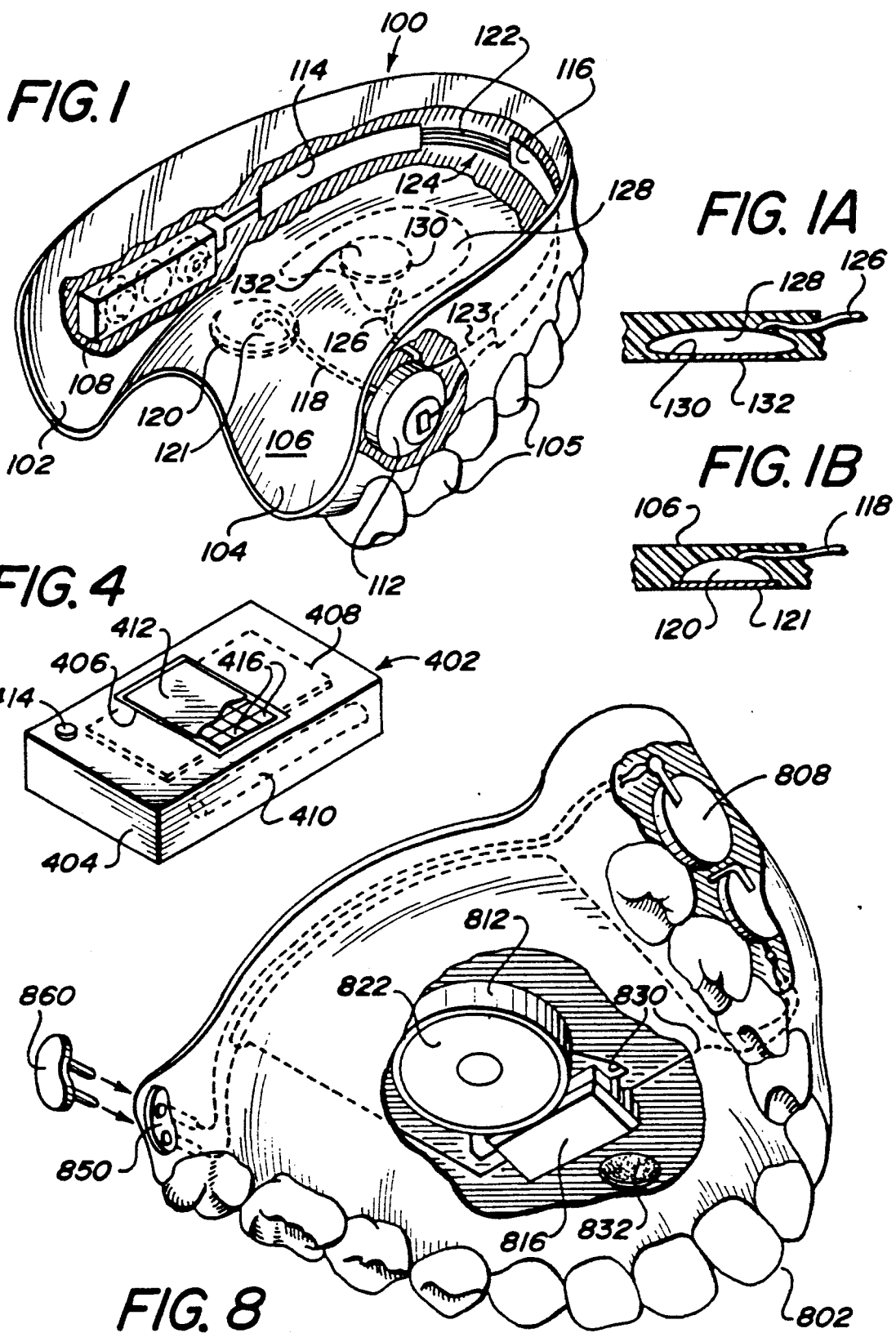

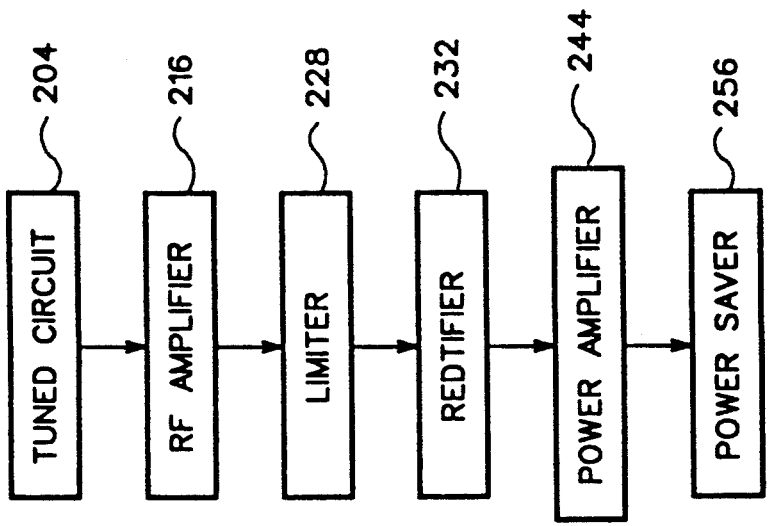
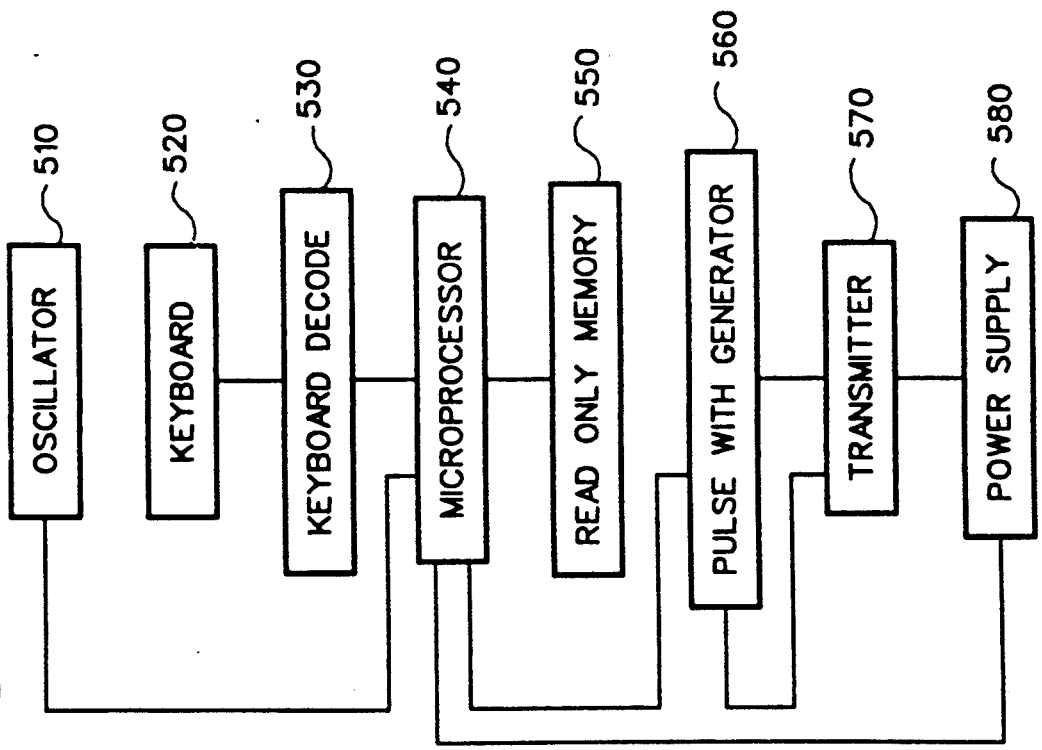

ARTIFICIAL LARYNX

BACKGROUND OF THE INVENTION

(1) Field of the Invention

The present invention relates to the field of sound-producing prosthetic devices for use by laryngectomized patients and more particularly to the reproduction by electronic-type artificial larynxes of natural sounding voice tones.

(2) Description of the Prior Art

It is frequently necessary to remove the larynx, or so-called voice box, by surgical procedures due to malignant growths in the larynx itself or adjacent tissues. With removal of the larynx and its component vocal cords, access of the trachea to air is necessary and a hole, or stoma, is, therefore, formed in the neck and the trachea is sewn directly to the tissues surrounding such stoma. Thereafter, the patient breaths through the stoma bypassing the upper respiratory track, including the mouth. Since the larynx normally reproduces voice tones or sounds by vibration of its membranes or vocal cords as air passes between these membranes while they are held in a tensed condition, a laryngectomy patient has no further ability to produce natural voice tones. In addition, no air can pass from the larynx through the mouth to be formed into various articulated speech tones, or even whispered speech, which does not normally require the use of a voice tone. Consequently, no speech whatsoever is possible for a laryngectomy patient, except so-called esophageal speech, which relies upon air passed from the stomach in a sort of belch after swallowing air. Such esophageal derived air can be formed into words, lacking, however, the normal voice tone, although vibration of the esophagus does produce a somewhat different tone, rather akin to belching. Such esophageal tone can be articulated into words by the lips, tongue and teeth. Esophageal speech is difficult and time consuming, both to learn and to practice, as well as difficult for others to understand without considerable experience and interpretation. Consequently, various artificial tone-producing devices have been developed in the past to provide a voice tone for articulation by the lips, tongue and teeth into speech either prior to a patient being able to learn esophageal speech or as a complete substitute for esophageal speech in public communication.

A large number of devices for producing artificial voice tones which can be shaped by a post laryngectomy patient into recognizable speech have been produced in the past. Such devices are generally referred to as artificial larynxes. For example, one of the very early artificial larynxes is disclosed in U.S. Pat. No. 1,901,433 issued Mar. 14, 1933 to G. W. Burchett. The artificial voice tone of Burchett was produced by a hand-held electrical tone generator which conducted the tone through a tube into the mouth of the laryngectomy patient where it could by movement of the mouth structures, be formed into at least somewhat intelligible voice sounds. The pitch of the sound could be controlled by means of a button on the tone generator. The Burchett device, like many later devices, suffered from poor reproducibility of voice sounds and was objectionable because of its high visibility, which visibility distracted others from trying to understand what was being said and embarrassed the user. Several more sophisticated devices of the same nature were developed by the Bell Telephone Laboratories and disclosed in U.S. Pat. Nos. 2,041,487 and 2,056,295 in 1936 and U.S. Pat. No. 2,202,467 in 1940 to Riesz.

In 1942 the use of a receiver held in the mouth to produce a potential voice tone was disclosed by G. M. Wright in U.S. Pat. No. 2,273,077. The receiver was connected to an external amplifier by an electrical wire. The Wright device also could use a tone transmitting tube and was used primarily for reproducing unusual voice tones, for example, in broadcasting and motion pictures, by persons having normal speech apparatus.

In 1942 G. M. Wright also patented one of the first artificial larynxes to apply voice tones against the throat in U.S. Pat. No. 2,273,078. Since that time, the Wright device and adaptations thereof have become one of the prime artificial larynxes in use. The Wright device included high and low frequency transducers to apply tones through the skin. Many of these devices have been hand held, as shown in U.S. Pat. No. 3,072,745 to H. L. Barny assigned to Bell Telephone Laboratories. Barney controlled the pitch of the tone produced by use of a rheostat over a spectrum said to approach natural speech tones.

In 1958, H. K. Cooper patented the use of a dental prosthesis or denture to contain an emitter or speaker, as shown in U.S. Pat. No. 2,862,209. Cooper formed artificial voice tones in his emitter at one side of the denture and conducted such tones through one or more resonating passages in the denture, at least one of which opened to a wider resonant chamber. It was disclosed by Cooper that higher frequency sound would tend to follow the narrower passage while lower frequencies would tend to follow the wider passage or resonating chamber. Conductors extended from the denture in the mouth to an energy source or controller carried in the user's pocket. The use of an electroacoustical transducer mounted in a denture with energy to operate such transducer being supplied through a wire leading into the mouth was also discussed by Barney, mentioned above, in his application filed in 1959 and issued as a patent in 1963.

Also in 1963, the use of a mouth controlled switch for an artificial larynx was disclosed in U.S. Pat. No. 3,084,221 to H. K. Cooper et al. This was followed in 1970 by U.S. Pat. No. 3,508,000 to C. M. Snyder who housed pressure transducers and the like in the mouth in artificial tooth structures.

U.S. Pat. No. 3,524,932, issued also in 1970 to F. F. Stucki and assigned to Lockheed Aircraft, disclosed the use of a number of transducers in the mouth for activation by the mouth structures during speech movements of the mouth parts. Small transmitters may be used to conduct these signals from the mouth to a receiver.

The use of rather sophisticated pitch and wave forms having the characteristics of a damped sinusoid closely approximating, it is said, the wave forms of normal speech, including numerous harmonics, is disclosed in U.S. Pat. No. 3,914,550 issued Oct. 21, 1975 to G. I. Cardwell.

U.S. Pat. No. 4,473,905 issued in 1984 to Katz et al. as well as several subsequent patents also assigned to Thomas Jefferson University disclose the use of sophisticated self-contained intraoral artificial larynxes or larynges comprising a power source, on-off controls, low power circuitry with acoustic and electrical amplifiers and small loud speakers. Switches for control of the voice tones provided by the devices are controlled by the tongue of the user. A similar device is disclosed by U.S. Pat. No. 4,706,292 issued in 1987 to W. L. Torgeson. Both these devices can produce sound which, after passing through the vocal tract of the user, is understandable and significantly better than possible with previously available devices. While both devices, therefore, are improvements over the previous state-of-the-art, both suffer from the fact that the speech sound produced, while largely understandable, does not have a natural sound and is therefore, frequently both an embarrassment to the speaker as well as to the one spoken to.

Finally, U.S. Pat. No. 4,571,739 issued in 1986 to J. A. Resnick discloses the provision of an artificial larynx in which the individual self-contained elements are contained not in the base of a denture, but in artificial teeth attached to such denture thus allegedly providing additional room permitting larger elements and better sound reproduction or articulation. Switches for the unit are positioned upon the backs of preferably the front teeth on the unit or those of the user him or herself. The speech sounds produced, however, still leave much to be desired.

There has been and continues to be, therefore, a need for an unobtrusive artificial larynx which can produce more natural sounding speech tones, the use of which can be learned quickly and easily and which can produce reproducible speech sounds more reliably and easily.

The sound of the human voice starts with a so-called glottal pulse formed as the larynx opens and closes releasing a puff of air. This puff of air can be described in physical terms as the number of cubic centimeters of air passing through the open larynx as a function of time, or the volume velocity as a function of time. Various Fourier components of the volume velocity contribute to the resulting sound wave which is eventually radiated from the mouth and nose. The glottal pulse sound wave is shaped by the vocal tract formed by the mouth, tongue, lips, teeth and nasal tract. This process is described in the book *Speech Analysis and Perception,* Flanagan, J. L. (1972) (Springer, New York) and more recently, in the article by Dennis and Laura Klatt entitled "Analysis, synthesis and perception of voice quality variations among female and male talkers" which appeared in the "Journal of the Acoustical Society of America" in February 1990, pages 820-857. To create natural sounding speech, therefore, an artificial larynx should produce a glottal pulse which duplicates the elements of the natural glottal pulse which contribute to the formation of audible sound.

The second element which contributes to natural sounding speech is the ability of the speaker to start and stop the glottal pulsing under his own control. The control of starting and stopping of sounds is as important to intelligible speech as is the continuation of the sounds. This starting and stopping of speech can occur at rates as fast as five times per second or 200 milliseconds per start/stop cycle. Therefore, the second requirement in producing natural speech sounds is to provide a means whereby the user of the artificial larynx can start and stop the sounds up to five times per second.

In addition to being able to initiate vibration of the larynx to form a voice tone, a natural speaker is able to alter the constriction of or the tension in the larynx to change the frequency of the basic repetition of the glottal pulse. The vibratory opening and closing can range for a human male from 75 to 250 times per second in normal speech. Typical male repetition rates are about 125 times per second. Human females typically have a normal frequency almost twice as high. If one takes singing into account, the range of vibratory frequencies is even wider. Therefore, the third requirement for producing natural speech is to provide a means by which the user of the artificial larynx can change the frequency of vibration in a range typically between 75 and 250 cycles per second for a male and from 150 to 500 cycles per second for a female.

A third element of natural speech is the inclusion of the fricative sounds caused by air rushing past a closing or almost closed constriction in the vocal tract. For example, the "s" sound is produced by placing the tongue behind the teeth and forcing air past the closure producing high frequency random noise. The "f" sound is produced by forcing air past a constriction formed by the lips. It has been observed that although laryngectomees do not breath through their mouths, they can collect air in the mouth and throat cavity and expel it by muscle contraction. This limited source of air flow is sufficient for forming fricative sounds in speech and has not been included in the current model of the artificial larynx. Further studies are under way to see if the inclusion of an artificial fricative makes learning to use the larynx easier or more difficult.

A fourth element of natural speech is the ability to change loudness and create emphasis on various tones. Changing the loudness of the speech sound realistically requires changing the frequency structure of the sound as well as increasing the absolute level of the original sound, i.e., it is more involved than merely linearly changing the sound level as would occur if one turned up the volume control knob on a radio. Accordingly, it would be desirable for an artificial larynx to incorporate a means for rapidly and independently changing the loudness and tonal quality of the sound in a realistic sounding manner.

A fifth element of natural speech is the ability to change tonal quality. Tonal quality is related to the ability to differentiate between the harmonic content of two sounds produced at the same fundamental frequency. Some speakers sound mellow and others sound shrill even though the fundamental frequency of the tones is the same. This difference in sound is due to differences in the harmonic content of the tones.

A sixth element of natural sounding speech is the inclusion of random noise in the higher frequency regions of speech sound production. This aspiration noise is different from the formation of fricatives in that the constriction is formed at the larynx itself and not a separate place in the vocal tract, and it accompanies normal vowel production. Accordingly, it would be desirable for an artificial larynx to include means for producing random noise such as aspiration noise.

A seventh element of natural speech is the slight random variation of the basic repetition rate of the fundamental tones. Studies have indicated that pseudorandom variation of tones as much as 0.5% of frequency accompanies natural speech and the inclusion of this random frequency variation reduces the "mechanical" nature of speech produced by an artificial larynx.

An eighth element of natural speech is the occasional absence of pulses as a speaker talks at lower volume or lower frequency, typically at the ending of phrases or sentences. Often every second pulse is absent or reduced in amplitude. This effect is called diplophonia. A natural sounding voice, therefore, should include a means of duplicating, under user control, some diplophonic sounds.

A ninth element of importance in human speech is the ability to whisper. Although this mode of speaking is different in many respects from normal speech, it still presents an important mode of speech which can assume some importance to the speaker.

Although the foregoing elements of natural speech have been long understood, none of the above cited prior references address these important issues As indicated above, therefore, there has been a need for an artificial larynx that will provide more natural sounding speech. More particularly, there has been a need for an artificial larynx that both addresses and solves all or at least most of these problems in a commercially acceptable manner which allows the creation of an artificial larynx capable of producing natural speech for the first time.

OBJECTS OF THE INVENTION

It is an object of this invention, therefore, to provide an efficient, practical artificial larynx which provides a natural sounding voice tone.

It is a further object of the invention to allow the user to provide and control glottal sounds which when shaped by the oral cavity, produce natural sounding speech.

It is a still further object of the invention to provide an artificial larynx which is effective in producing a natural sounding voice tone, but which can be mastered relatively quickly and easily.

It is a still further object of the invention to provide an artificial larynx with a sensitive control of the important functions of normal speech easily controllable by the user with a minimum of difficulty and training.

It is a still further object of the invention to provide an artificial larynx which combines in its operation each of the most important factors contributing to the normal sound of human speech.

It is a still further object of the invention to provide a control for an otherwise self-contained artificial larynx which can be operated in multiple modes by a portion of the human body having superior sensitivity and adaptability.

It is a still further object of the invention to provide a practical and effective hand-held control for an otherwise self-contained oral-type artificial larynx.

It is a still further object of the invention to provide am effective hand-held control unit easily operated in multiple modes for an otherwise self-contained artificial larynx contained entirely in the mouth and communicating with the control unit via electromagnetic wireless communication.

It is a still further object of the invention to provide an artificial larynx which combines ability to control the exact beginning and ending of artificial glottal pulses in very small time intervals along with the frequency of the tone of the pulses in the range of frequency representing both male and female voices.

It is a still further object of the invention to provide an artificial larynx which combines means to change the loudness of the artificial tone along with changes in frequency.

It is a still further object of the invention to provide an artificial larynx which combines the ability to change tonal quality, provide random noise in the tone, vary the repetition rate of fundamental tones in a pseudorandom manner within certain limited ranges and to eliminate occasional glottal pulses, particularly at lower frequencies.

It is a still further object of the invention to provide an artificial larynx having an artificial whisper mode of operation.

It is a still further object of the invention to allow the user to produce a natural sounding whispering, when desired.

It is a still further object of the invention to provide a small, easily carried device which provides economical use of power.

It is a still further object of the invention to provide a design which allows easy learning of the finger or thumb motions which control the sounds emitted.

It is a still further object of the invention to provide an artificial larynx including programmable digital computer means for controlling the production of artificial voice tones.

It is a still further object of the invention to provide an artificial larynx including the use of a digital wave form in connection with a programmed speech simulation.

It is a still further object of the invention to provide a self-contained artificial larynx in a dental prosthesis incorporating a loud speaker associated with a speaker back cavity; a venting port and a membrane for transmitting sound from the venting port to the environment.

It is a still further object of the invention to provide an artificial larynx with a programmable digital computer system operated by a computer program control.

Other objects and advantages of the invention will become evident by reference to the following specification and description together with the appended drawing figures.

SUMMARY OF THE INVENTION

The present invention provides a novel, self-contained artificial larynx comprising two separate units; a control unit held preferably in the hand and an acoustic unit worn in the mouth, preferably in a dental prosthesis. Both units are battery powered.

The preferred embodiment of the hand-held unit contains the following elements: a battery or other power means, a keyboard or finger control unit, a microprocessor system and a transmitter unit. The preferred embodiment of the oral unit comprises: a dental prosthesis, a battery or other power means, a loud speaker, a loudspeaker back cavity, a venting port, a membrane for transmitting sound, a receiver and a power amplifier unit.

The invention, through a careful shaping of artificial voice tones, including one or more of the pitch and loudness, control of pulse length, repetition of the pulse length, tonal quality, the inclusion of random noise, random variation in the repetition rate and the deletion of pulses, is able, by the use of a microprocessor-operated tone control, to provide a natural sounding voice simulation from an artificial electronically operated larynx.

The small keyboard or hand digit controlled unit which is operated typically by either thumb or finger movement, provides a series of frequencies and loudness levels at the will of the speaker by depression of various keys arranged in several rows on the keyboard or digital contact control surface. The sound tone is started or stopped by depression or release of the keys or contacts. The keyboard allows changing from one combination of frequency and loudness represented by a particular point on the keyboard to another combination of frequency and loudness represented by another particular point on the keyboard, either in steps or continuously depending upon whether pressure is maintained by a sliding motion of the thumb or finger across the keyboard or whether the thumb or finger and particularly the thumb skips from one location to another.

A microprocessor system is used for control of the tone or voice sound provided by the unit. Preferably, a computer program provides most of the functional control of the operation of the artificial larynx including the creation of the electrical waveform for the tone pulses, changing the repetition rate of such pulses, changing the volume of the tone pulses and their tonal structure, changing the tonal nature of the sound at the same frequency, supplying random variation to the repetition rate of pulses, providing aspiration sounds, and providing diplophonia or deletion of tone pulses. In addition, the computer program preferably contains provision for reducing the power drain upon the unit by powering down the unit in periods of time when computational power is not required. The dental prosthetic preferred is either a full upper denture for laryngectomees without natural upper teeth, or a dental retainer for those with their own teeth. The loud speaker preferably features a high acoustic output in the range between 300 and 700 hz with a closed back configuration and low electric power consumption.

In an alternate embodiment of the invention, the keyboard or digital contact control surface may be replaced by a different man/machine interface. Such interface could, for example, comprise a joystick, a trackball, a force sensing resistor linear potentiometer, or any other small single hand supportable man/machine interface device capable of representing a matrix of sound frequency and volume. Various arrangements and combinations of such matrix of sound are within the scope of the invention.

BRIEF DESCRIPTION OF THE DRAWINGS

FIG. 1 is an isometric partially broken away view of the oral unit of the invention showing a speaker and associated structures, a battery, a receiver and a power amplifier plus associated electronics mounted in a conventional dental prosthetic.

FIG. 1A is a cross-sectional view of a portion of the palatal arch of a prosthesis such as shown in FIG. 1 illustrating the arrangement of a speaker back pressure cavity in such prosthesis.

FIG. 1B is a cross-sectional view of a portion of the palatal arch of a prosthesis such as shown in FIG. 1 illustrating the arrangement of a sound outlet in such prosthesis.

FIG. 2 is a block diagram of the electronic circuit for the oral unit shown in FIG. 1.

FIG. 4 is a diagrammatic isometric view of the control unit of the invention illustrating a mechanical housing, a keyboard, an internal circuit board, and an internal ferrite antenna which radiates the output pulse width carrier signal to the oral unit.

FIG. 5 is a block diagram of the electronic circuit for the control unit.

FIG. 8 is an isometric partially broken-away view of the inside of a prosthesis in accordance with the present invention incorporating a centrally mounted speaker.

DESCRIPTION OF THE PREFERRED EMBODIMENTS

Figure 3A:
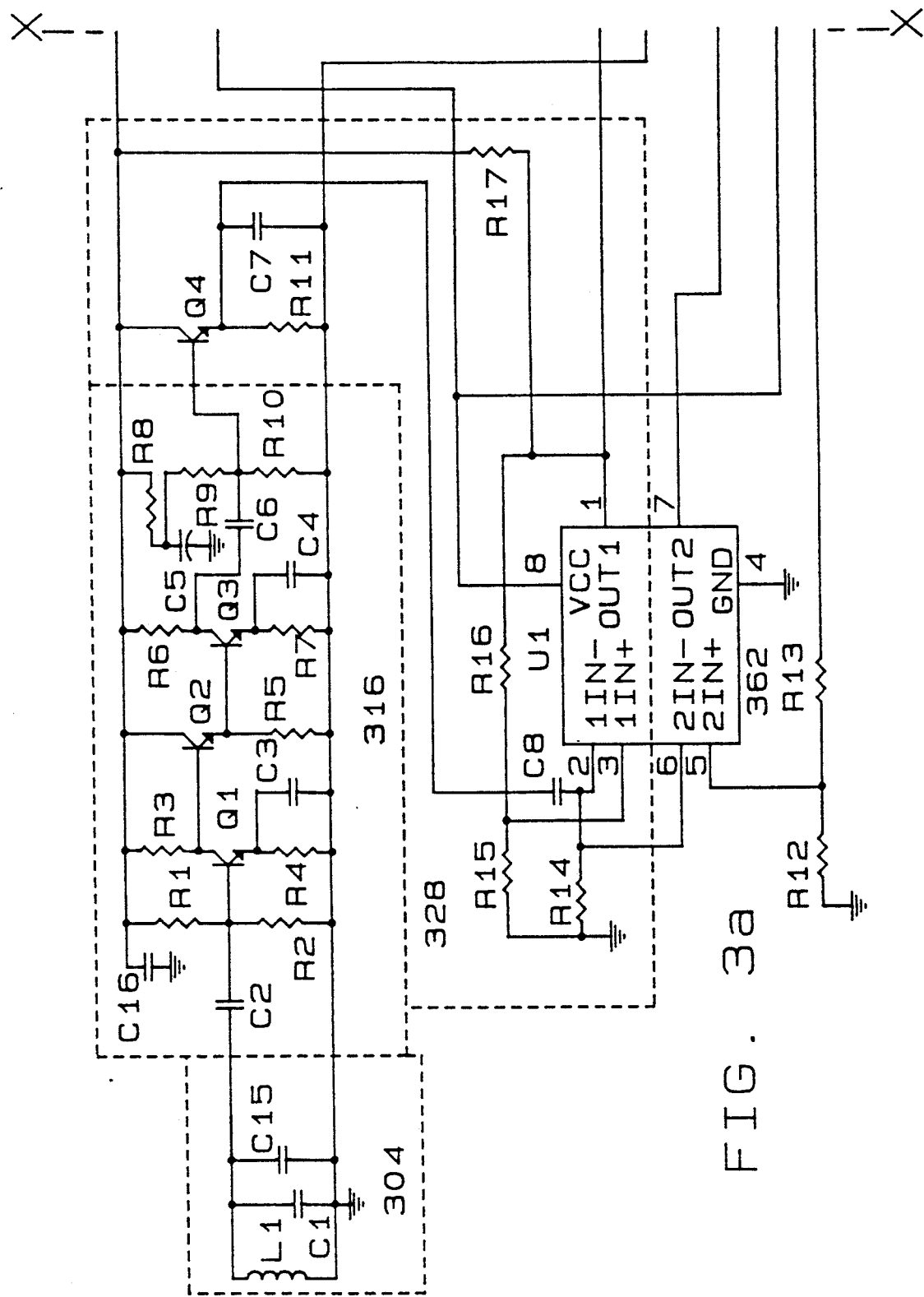
FIGS. 3a and 3b are two adjacent connected portions of a unitary circuit diagram of a preferred electronic circuit for the oral unit.

While specific forms of the present invention described hereinafter have been selected for the purposes of illustration, one of ordinary skill in the art will recognize that various departures may be made from the examples set forth herein without departing from the scope of the invention which is defined more particularly in the appended claims.

As indicated previously, while prior workers in the art have developed a number of fairly sophisticated artificial larynxes, none has been able to provide really natural sounding voice tones produced within or conducted into the mouth for modification by the mouth structures, including the lips, tongue, teeth and also the nasal cavity, to produce a natural-sounding voice for a laryngectomy patient. The present inventor, however, has, by a careful arrangement and combination of functions and parts, been able to provide a very natural-sounding voice tone that is, furthermore, conveniently and easily controlled, as well as learned, by the laryngectomy patient.

The artificial larynx of the present invention generally comprises a unit worn in the mouth, referred to as the oral unit, and a unit held in the hand, referred to as the control unit. The oral unit is comprised of a prosthetic means for mounting the artificial larynx in the oral cavity, a power source mounted on the prosthetic means, a receiver unit for capturing radio frequency signals transmitted from the control unit, and an amplifier for translating the received radio frequency signals into audio frequency electrical power for a loud speaker mounted on the unit, plus various acoustic elements used in association with the loud speaker, including a loud speaker back cavity, a venting port and a membrane for transmitting the sound.

A preferred embodiment of the hand-held unit contains a battery or other power means, a keyboard, a microprocessor system and a transmitter unit. The keyboard has a preferably small dimension, approximately 1" by 0.5" in area, and is controlled typically by thumb movement. However, it can also be controlled by finger movement. The keyboard can be represented as a two-axis system, a forward axis and a sideways axis. Moving the thumb sideways can access typically or preferably up to eight separate frequency values and moving the thumb forward can preferably access up to four separate loudness levels. Thus, thirty-two separate locations control thirty-two separate combinations of frequency and loudness. As long as the keyboard is depressed, a sound will be generated by the unit. When the keyboard is released, the sound stops. The keyboard allows changing from one point or combination of frequency and loudness to another either in steps or continuously depending on whether pressure is maintained in a sliding motion of the thumb across the keyboard or whether the thumb skips from one location to another. It is within the scope of the invention to provide a button-type switch that can move in an xy coordinate plane over the digital contact control surface depressed by the thumb or a finger.

The microprocessor system incorporates an eight bit CMOS microprocessor, some read only memory (ROM) for program storage, and an oscillator providing timing signals and associated control support chips. The computer program provides most of the control functionality of the device including the creation of the electrical waveform for the glottal pulse, changing the repetition rate of the glottal pulse, changing the volume of the glottal pulse and its tonal structure, changing the tonal nature of the sound at the same frequency, providing random variation in the repetition rate of pulses, providing aspiration sounds, and providing diplophonia or deletion of certain pulses. The use of a digital waveform allows correction for non-linearities in the acoustic and electric systems to recreate accurately the glottal pulse over a wide range of frequencies and volumes. In addition, it contains provision for reducing the power drain by powering down the unit in periods of time when computational power is not required. Also, the microcontroller decodes and debounce the keyboard.

The transmitter unit employs a pulse width modulation system to send information to the receiver. The microprocessor provides an on-gating signal from an oscillator running typically at 3 megahertz. The on signal allows a pulse of three Mhz oscillations to be transmitted to the receiver. The transmitter uses a ferrite rod wrapped with wire to generate a changing magnetic field which radiates the signal to the mouth based receiver.

The oral unit is comprised of a dental prosthetic, a loud speaker, a battery, a receiver, and a power amplifier. The dental prosthetic preferred is either a full upper denture for laryngectomees without natural upper teeth, or a dental retainer for those with their own teeth. The loud speaker has been specially developed for this application and features a high acoustic output in the range between 300 and 700 hz with a closed back configuration and low electric power consumption. The back cavity of the speaker is typically one (1) to three (3) cubic centimeters in volume. The speaker emits the sound to the mouth through a diaphragm, which is designed to transmit sound out, but prevent moisture, saliva, food and bacteria from entering the sound path or internals. In addition, the back cavity of the speaker must be vented to the area between the speaker and the diaphragm and a vent is required to the mouth to allow pressure equalization. The vent to the mouth should pass air, but not bacteria, saliva and the like. The circuit and loud speaker will preferably, at maximum volume, draw about 30 milliamperes of current. Commercially available rechargeable batteries preferably supply 30 milliamperehours of current which is sufficient to enable about one hour of continuous speech sound at maximum volume between battery charges.

The receiver has a tuned detecting circuit, a radio frequency amplifier, a signal limiter and demodulator, and a power amplifier. The tuned circuit is formed from an inductor and capacitor tuned to resonate at 3 Mhz. The signal goes to an amplifier with a voltage gain of about 1000. High impedance levels are used to minimize power drain. The amplified radio frequency contains pulse width information which is detected and put through a limiter to minimize signal distortion from impedance or level changes in the signal channel. This pulse width information is demodulated and goes to a power amplifier to drive the small loud speaker. The power amplifier is comprised of an integrated circuit which ordinarily finds application in small battery-powered radios.

In an alternate embodiment of the present invention, the keyboard may be replaced as indicated previously by a different type of man-machine interface. Such interface could be a joystick, a trackball, a force-sensing resistor linear potentiometer, or any other small single hand supportable man-machine interface device capable of representing a matrix of sound frequency and volume. Various arrangements of the matrix are within the scope of the invention.

Referring now to FIG. 1, the preferred prosthetic means, shown partially broken away and designated generally 100, will be seen to comprise a conventional full upper dental prosthesis. The body of the dental prosthesis is formed from conventional dental prosthetic material, such as an acrylic polymer, which is shaped to fit comfortably in the mouth. This body is preferably formed to encapsulate all the electrical components of the preferred embodiment artificial larynx. While a large number of laryngectomees have full or partial upper dentures (false teeth), some laryngectomees retain their natural teeth. It will be readily evident to those skilled in the art that the artificial larynx could be mounted on or embedded within a partial dental prosthesis, a suitable dental retainer or other embodiments of the invention.

The dental prosthesis 100 shown in FIG. 1 includes two base sections 102 and 104 in which artificial teeth 105 are fixed, which bases 102 and 104 fit comfortably over the gums of the wearer with a palatal 106 arch between the base sections which fits against or in close proximity to the hard and soft palates of the wearer. Encapsulated within the acrylic or other plastic resin material of the prosthesis in the side above the base 102 are first batteries 108 which may typically include two to four (three are shown) rechargeable batteries mounted in series together. The necessary electrical circuits for detecting a radio frequency signal from the hand control, see FIG. 4, and amplifying such signal for operation of a speaker 112 are contained in a first and second electrical circuit assemblies 114 and 116. Such electrical circuits, which will be familiar to those skilled in the art of electronic signalling and receiving, amplify and rectify the radio frequency signal and transmit it to the speaker 112, which produces pulses or sound waves in the air within the speaker, which pulses are transmitted through speaker tube 118 to sound outlet 120 in the palatal arch 106 of the prosthesis 100. It will be understood the speaker or sound tube 118 will have a diameter and smooth interior surfaces that will not interfere with the transmission of sound pulses having fairly sophisticated frequency and pulse characteristics. The speaker or sound tube 118 preferably passes integrally through the body of the prosthesis, but may comprise a separate tube either embedded within the material of the prosthesis or external thereto. The two radio frequency handling circuits embodied in the circuit assemblies 114 and 116 can be referred to as a signal or combined signal circuit 124, the two circuits being connected by electrical wires 122.

The electrical circuit 124, as indicated, receives the radio frequency signals transmitted from the control unit through an internal antenna, not specifically shown. Typical transmission and receiving frequencies used in the invention are between 1 and 4 megahertz. The circuit 124 also amplifies and rectifies the radio frequency signal and provides the required electrical power to the loud speaker 112 to operate or vibrate such speaker. Electrical wires 123 connect the circuit 124 with the loud speaker 112. The loud speaker 112 is protected from moisture by a small rubber or other diaphragm 121 at the exit to the sound outlet 120. See in particular FIG. 1B. An artificial voice tone is conducted to the center of the mouth cavity near the upper palate by either a small rubber tube or the integral sound or speaker tube 118 as explained previously. The rubber or other flexible diaphragm 121 is positioned preferably on the inner or mouth side of the sound outlet 120 which sound outlet takes the form of an opening or cavity within the prosthetic material. The sound pressure oscillations, or waves, pass easily through the moving rubber diaphragm 121.

A tube or channel 126 also connects the back of speaker 112 to a back pressure cavity 128 typically 1 to 3 cubic centimeters in volume preferably within the body of the prosthesis 100. The larger the space provided behind the speaker, the less force is required to move the speaker diaphragm and the less power is as a consequence used to create sound. Changes in atmospheric pressure could alter the balance between the back pressure cavity and the air pressure in front of the speaker. Consequently, a venting port 130 to the mouth is required for proper pressure equalization. In addition, bacteria and saliva must be kept out of the internal volume of the back pressure cavity 128. A venting port made from or covered with fine Teflon filter material 132 has been provided for this purpose in the mouth side of the prosthesis. In addition to venting the rubber diaphragm 121, the speaker diaphragm must also be vented. It can be vented internally as with a 0.010 diameter hole or orifice through the speaker diaphragm.

The coupled system comprised of the hand-held transmitter and the radio receiver in the mouth uses pulse width modulation of a radio frequency signal to transmit the audio information necessary for driving the loud speaker. In a pulse width modulation system, the radio frequency carries or codes the amplitude information in accordance with the width of the signal pulse transmitted. A longer pulse indicates or codes for a higher voltage electrical signal. Typically a pulse width modulation system includes a signal detector, an amplifier, a limiter, and an integrator. The signal detector is sensitive only to the signal carrier frequency with amplitude above 50 microvolts. The amplifier makes the carrier large enough to be limited and the integrator converts the pulse width to a voltage level signal. As will be understood, other modulation systems such as an FM system might also be used.

Referring now to FIG. 2, which shows diagrammatically the principal elements of the combined circuits 124, a high Q tuned circuit 204 detects any signal present and is designed to be sensitive to changing electromagnetic fields. The detected signal is directed to a radio frequency amplifier 216 which has a gain preferably of about 1000. The amplified radio frequency signal is then directed to a rectifier section 232 via a limiter 228 which defines the signal to be detected. The output of the rectifier signal may alternatively be directed to a comparator apparatus, not shown, set to detect a signal of about 50 millivolts. When a signal above 50 millivolts is present, the comparator output is active. With no signal present, the comparator output is inactive and set to the value of the positive voltage supply, Vcc. The comparator in such case fulfills the limiting function of the circuit 228. This signal is then demodulated in the audio amplifier 244 to create the linear output from the power amplifier which provides a low impedance voltage source for the loud speaker 112 shown in FIG. 1. Also shown on the block diagram of FIG. 2 is a power saving circuit 256 which uses the other half of the comparator, if used, to turn on and off the power amplifier in the presence and absence of a signal respectively.

Figure 3B:
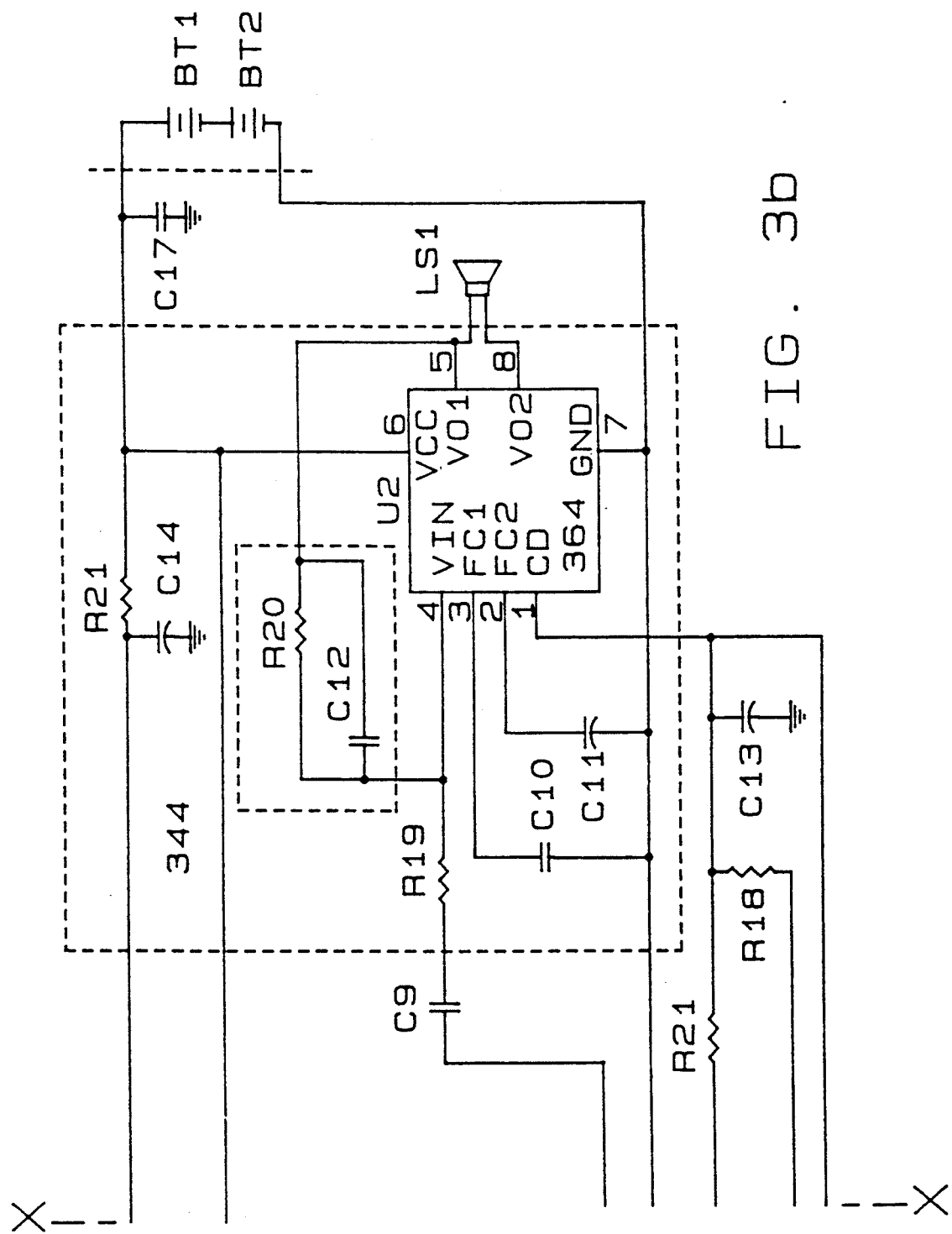
Figure 6A:
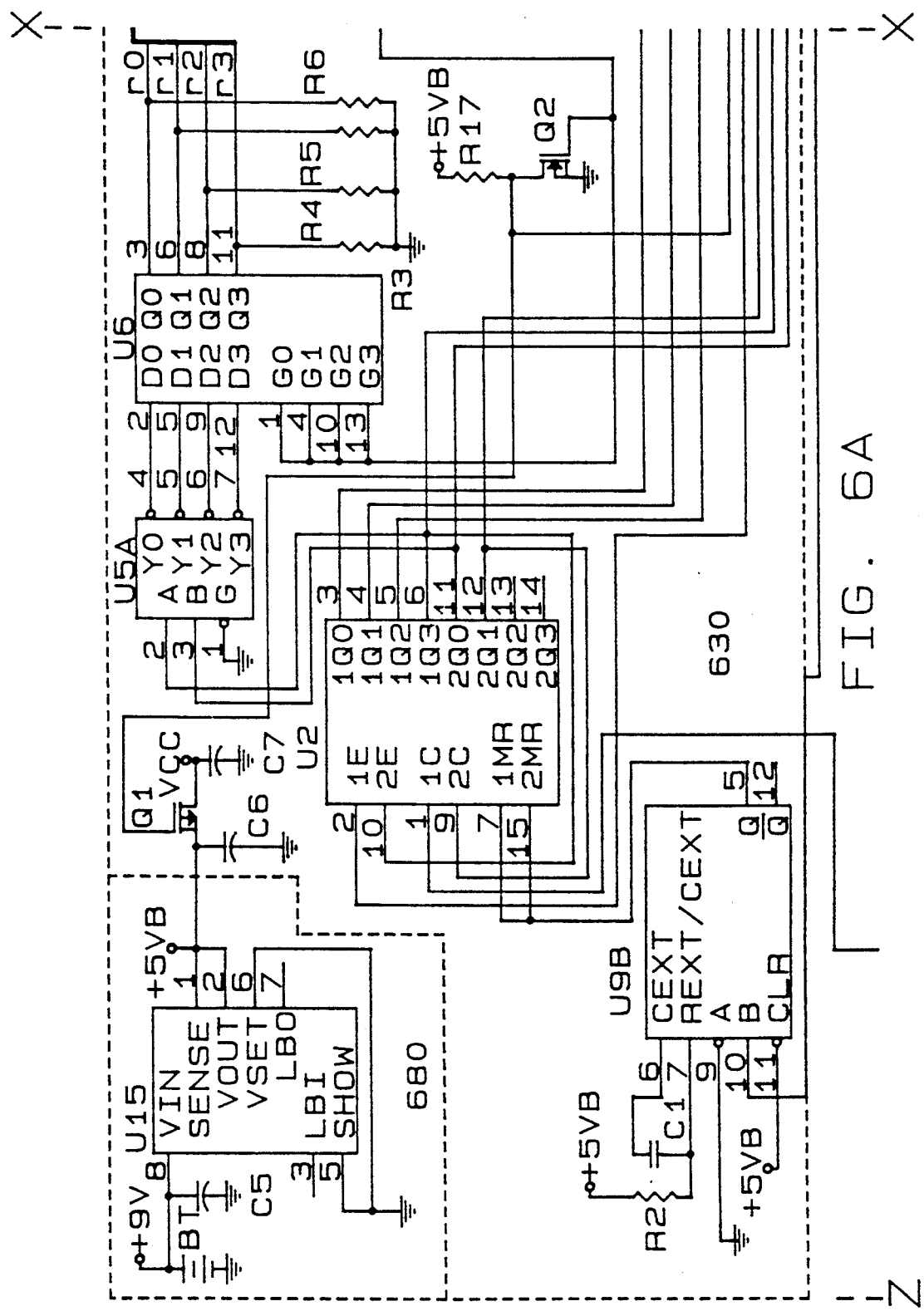
FIGS. 6A, 6B, 6C and 6D are four adjacent connected portions of a unitary circuit diagram or schematic of the control unit electronic circuit.
Figure 6B:
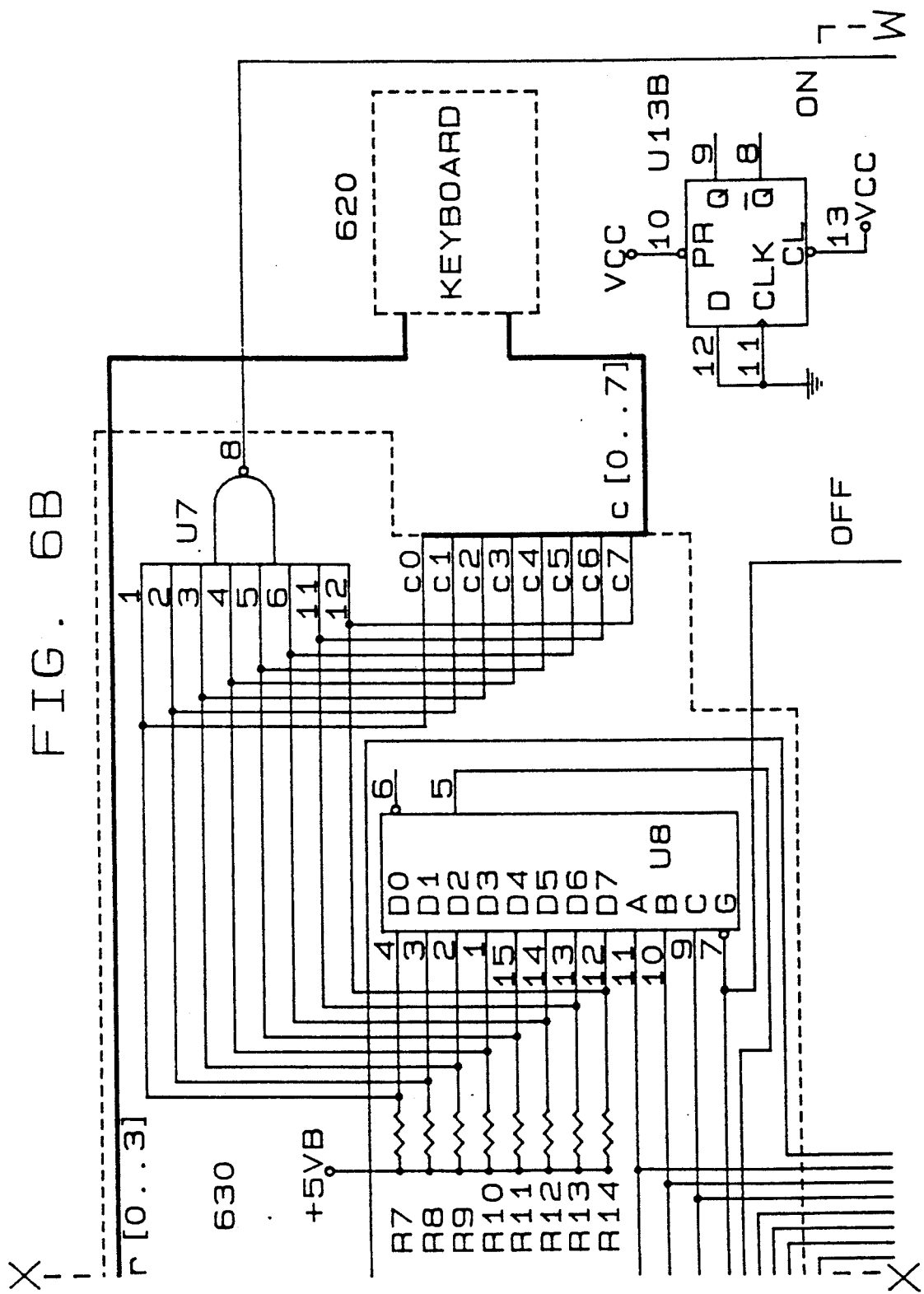
Figure 6C:
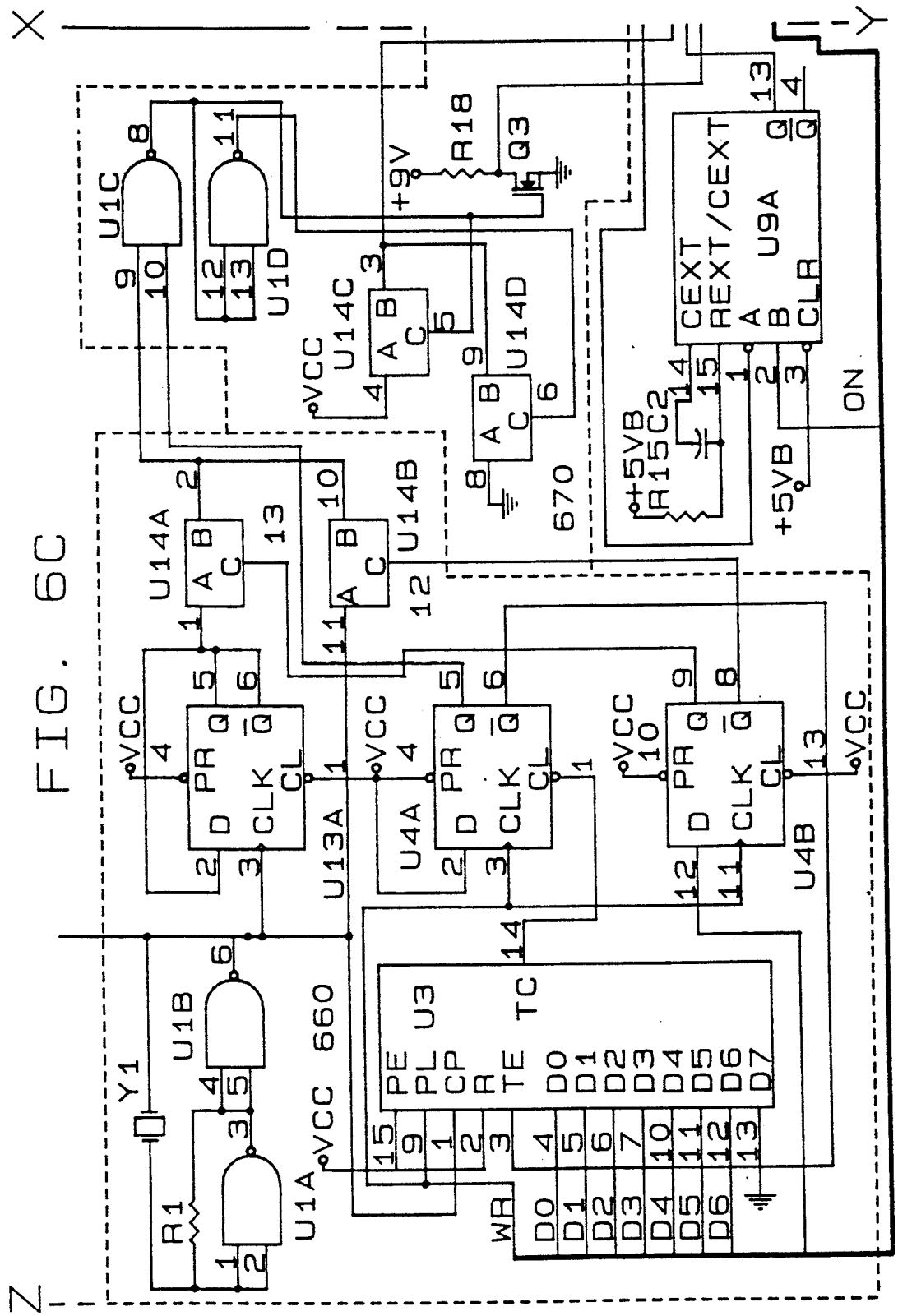
Figure 6D:
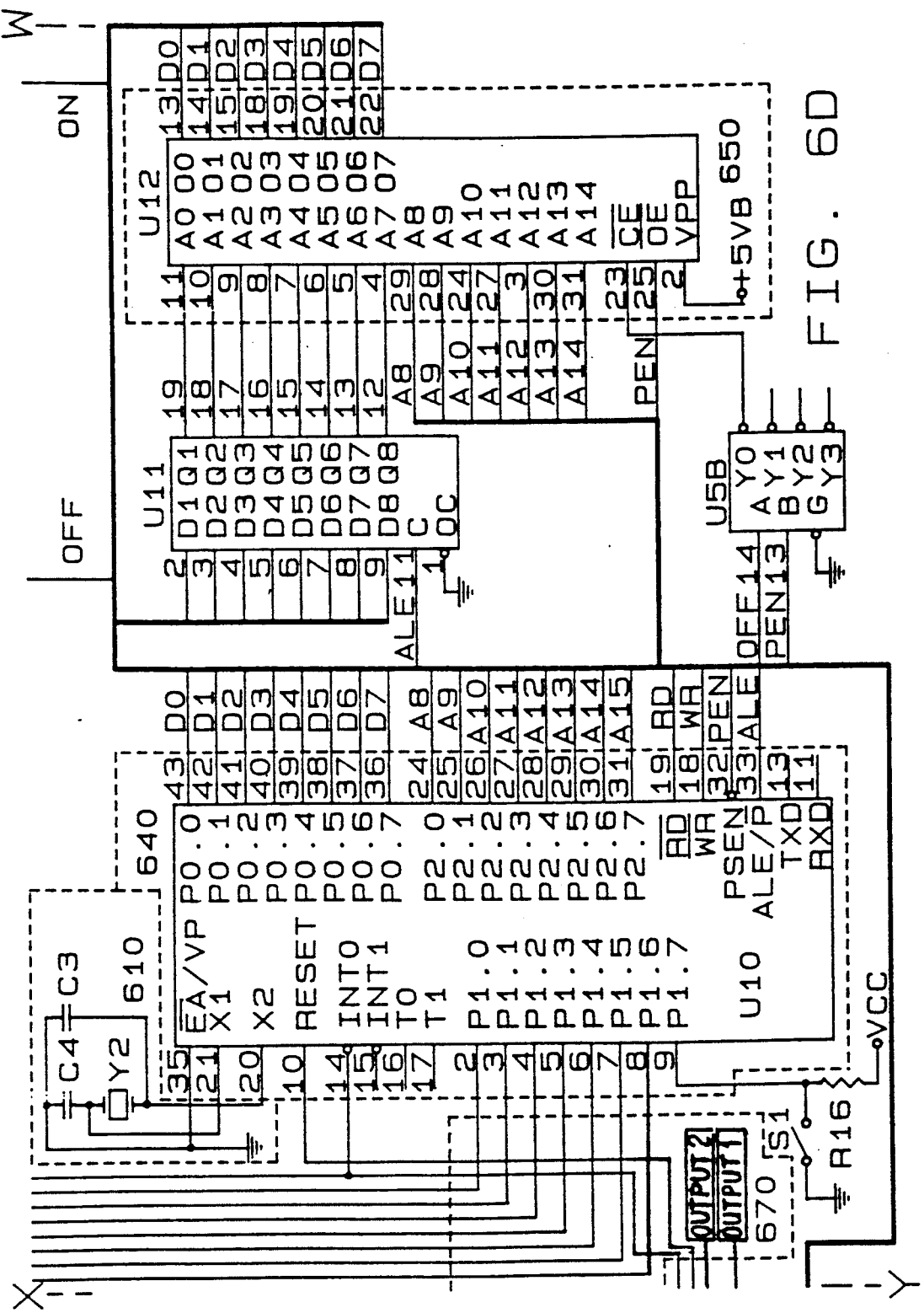

Referring now to FIG. 3, or combined FIGS. 3a and 3b, there are provided further details of the broad circuits shown in block diagram form in FIG. 2. The broad circuit components shown in FIG. 2 and numbered with reference numerals in the two hundred series have been broadly outlined or set off in the circuit diagram of FIG. 3 (FIGS. 3a and 3b) with dotted lines and identified with similar reference numerals in the three-hundred series, i.e. the tuned circuit identified in FIG. 2 by the reference numeral 204 is identified in FIG. 3a by the reference numeral 304, while the RF amplifier identified in FIG. 2 by the reference numeral 216 is identified in FIG. 3a by the reference numeral 316 and so forth. The individual electrical components of the circuit diagram are identified by conventional electronic-type reference numerals, i.e. with an initial letter designation indicating broadly the general type of components, followed by a numerical representation of the identity of that particular component on the circuit diagram.

The initial tuned circuit in FIGS. 3a and 3b is comprised of a 47 microhenry inductor L1 and a 47 picofarad capacitor C1 which resonates at a frequency of about 3 megahertz. The inductor L1, besides being part of the tuned circuit 304 shown also in the block diagram of FIG. 2, detects changing electromagnetic fields and therefore makes a useful signal detector. The signal goes to the radio frequency amplifier 316 which is comprised of a transistor Q1 operating as a common emitter amplifier with signal bypass capacitor C3 in the emitter section. This amplifier is followed by a common collector transistor Q2 (emitter follower) which reduces the effect of Miller capacitance on the next amplifier section by lowering the signal impedance.

Other conventional electronic components are shown in FIGS. 3a and 3b, the use and function of which will be readily understandable to those skilled in the art. Typical operating values for the components shown in the circuit diagram of FIG. 3 are set forth in Table I below, which is arranged as a listing of parts in which the first column indicates the quantity or number of components with particular characteristics used in the circuit diagram of FIGS. 3a and 3b the second column provides the reference numeral by which such components are identified in FIG. 3, and the third column provides the specifications for the particular part or components. As will be recognized, an electronics engineer or technician will, by reference to the circuit diagram of FIGS. 3a and 3b and Table I, be readily able to provide an operating circuit in accordance with the invention as diagramed in FIG. 3, or combined FIGS. 3a and 3b.

TABLE I

PARTS SPECIFICATIONS FOR COMPONENTS OF ORAL UNIT CIRCUIT

| Quantity of Component | Identifying Component Reference Numerals | Electrical Specifications |
|---|---|---|
| 2 | BT1, BT2 | 1.5V |
| 1 | C1 | 47pF |
| 1 | C2 | 220pF |

TABLE I-continued
PARTS SPECIFICATIONS FOR COMPONENTS OF ORAL UNIT CIRCUIT

| Quantity of Component | Identifying Component Reference Numerals | Electrical Specifications |
|---|---|---|
| 2 | C3, C4 | 470pF |
| 3 | C5, C11, C13 | 4.7uF |
| 1 | C6 | 100pF |
| 1 | C7 | 270pF |
| 5 | C8, C9, C10, C16, C17 | 0.1uF |
| 1 | C12 | 2200pF |
| 1 | C14 | 15uF |
| 1 | C15* | 0..10pF |
| 1 | L1 | 47uH |
| 1 | LS1 | SPEAKER |
| 4 | Q1, Q2, Q3, Q4 | 931 |
| 3 | R1, R2, R9 | 100k |
| 3 | R3, R4, R6 | 10k |
| 2 | R5, R11 | 39k |
| 1 | R7 | 5.1k |
| 1 | R8 | 330k |
| 1 | R10 | 390k |
| 5 | R12, R14, R15, R17, R18 | 22k |
| 2 | R13, R16 | 4.7M |
| 2 | R19, R20 | 220k |
| 1 | R21 | 3.3k |
| 1 | R21 | 470 |
| 1 | U1 | TLC 352C |
| 1 | U1 | MC 34119 |

The last section of the rf amplifier 316 shown in FIG. 3a has a rectifying output. This rectified output detects the pulse envelope shape of the signal. The envelope shape should be amplitude independent for accurate transmission of the pulse width information. Therefore, following the rectifier is a comparator indicated by the reference numeral 362 which is set to trigger at a signal level of about 50 millivolts. When the signal is above this level, the comparator output is active. When it is below this level, the comparator output is not active. This limiting action prevents signal amplitude changes from affecting the signal information.

The same comparator 362 is used to trigger the power up, power down modes of operation of the output amplifier. Appropriate rise and fall time constants are set in conjunction with the software pulse shape design to insure that the power amplifier 344 turning on and off does not occur in the middle of the pulse which would create a clicking sound.

The output from the limiter 228 shown in FIG. 2 and 328 outlined in FIG. 3a goes to the component 364 which is a small integrated circuit audio amplifier with feedback. The feedback is set to demodulate the signal and provide proper signal gain. The audio output goes to the loud speaker. The power up/down is controlled by the second comparator.

The hand-held control unit 402 shown diagrammatically in FIG. 4, is comprised of a mechanical housing 404 which incorporates a small keyboard 406, a circuit board 408 shown in outline within the housing 404, and a ferrite antenna 410, also shown in outline within the housing 404. A light-emitting diode 414 is also shown which serves to show low battery voltage with respect to a battery, not shown, also contained, however, in a portion of the hand control unit. The keyboard 406 typically has an area in which there are located keys 416 sensitive to the touch of a hand digit, typically the thumb. The size of the active area on the keyboard is preferably about 1 inch by 0.5 inch in size. Thus the control unit can be held in the palm of the hand and controlled easily by the thumb. The keyboard contains typically an eight column by four row matrix of 32 separately addressable keys. The keys are on 0.125 inch centers. Because of the large size of the thumb with respect to the key spacing, it is expected that several keys will be simultaneously addressed. The microprocessor circuit embodied in the circuit board 408 consequently preferably contains provisions for determining the intended key location as well as debouncing the keyboard. In the preferable arrangement, the individual keys are not directly contacted by hand digits, but are overlain by a flexible cloth covering or plastic membrane 412 which constitutes the actual structural surface contacted by the fingers and/or the thumb in operating or fingering the keyboard and through which the underlying keys 416 are activated by depression of the overlying membrane 412. Although the housing is shown for convenience of illustration in FIG. 4 with right angled edges, it will be understood that the edges may more preferably be rounded.

Computational circuitry on the circuit board in conjunction with the keyboard input pattern determines the width of the electromagnetic pulses which carry information concerning the artificial glottal pulse to be produced and the 3 Mhz carrier frequency is modulated accordingly. The carrier frequency pulses are transmitted from the ferrite rod antenna 410 to the receiving antenna of the oral unit.

Referring now to FIG. 5, the electronic circuits of the control unit 402 are seen to comprise an oscillator 510, a keyboard 520, a keyboard decoding circuit 530, a microprocessor 540, a read only memory 550, a pulse width generator 560, and a gated transmitter 570, the last two circuits 560 and 570 taken together being referred to as a pulse-width modulation transmitting system, and a power supply 580 in the form of an integrated circuit. Low power CMOS components typically are chosen to provide the logic functions for the circuit.

Referring to FIGS. 6A, 6B, 6C and 6D, there is shown a circuit diagram or schematic for the hand-held control of the invention. The broad circuit components shown in FIG. 5 and numbered with reference numerals in the five-hundred series have been broadly outlined or set off in the circuit diagram of FIG. 6, or combined FIGS. 6A, 6B, 6C and 6D, with dotted lines and identified with similar reference numerals in the six-hundred series, i.e. the oscillator 510 identified in FIG. 5 is identified in FIG. 6 by the reference numeral 610, while the keyboard or key system identified in FIG. 5 by the reference numeral 520 is identified in FIG. 6D by the reference numeral 620 and so forth. As in FIG. 3a and 3b, the individual electrical components of the circuit diagram are identified by conventional electronic-type reference numerals, i.e. with an initial letter designation indicating broadly the general type of component, followed by a numerical representation of the identity of that particular component on the current diagram.

Now referring to a preferred embodiment of the electronics of the hand control unit 402 as shown in FIG. 6, or combined FIGS. 6A, 6B, 6C and 6D, the 80C51 microcontroller U10 outlined as microprocessor 640 operates at a frequency of 12 Mhz which is provided by the crystal Y2 within the oscillator 610. The keyboard 620 is a row-column matrix unit with a decoding circuit 630. In the active mode, when one of the keys is depressed, the microcontroller makes an inquiry about the coordinates of that key during the time available at the end of a glottal pulse. For that purpose, the microcontroller sets a logical "1" on its output labeled "INTO" on the diagram. The one-shot multivibrator U9B shapes this signal into a positive pulse which resets the counter U2.

After that, the counter starts to increment due to the 3 Mhz pulses on its input 1C. The outputs 1Q0, 1Q1, 1Q2 stimulate the a column of the keyboard. The outputs 1Q3, 2Q0 provide stimuli through the decoder U5A and the buffer U6 on the rows r[1..3) of the keyboard. The active signal (logical "0") is applied consecutively to the rows.

Once the active signal is applied to the depressed key, it goes via that key and the associated column to the multiplexor U8. When the code of the column on the inputs A, B, or C of the integrated circuit U8 coincides with the number of the column being activated (D0..D7 of U8), the output Y of U8 goes to the logical "1" causing the counter U2 to stop incrementing. Thus the coordinates of the depressed key are fixed on the output of the counter U2. In its turn, the microcontroller reads these data via inputs P1.0, P1.1, P1.2, P1.4, P1.5, using them to determine the appropriate parameters of the glottal pulse.

As mentioned above, the microcontroller provides that determination at the end of each glottal pulse and if there is no key pressed, the counter U2 increments until a logical "1" on its output 2Q1 stops the counting. The same signal indicates this event to the microcontroller via input P1.3. Recognizing that, the microcontroller sets logical "0" on its "INTO" output and goes then to the power down mode. A logical "0" on "INTO" forces the buffer U6 to get high impedance outputs. Since no key is depressed, all inputs of U7 are logical "1". As soon as any key is pressed, a logical "0" from the appropriate row goes through that key on the input of U7, causing the output of U7 to go to a logical "1". In addition, the one-shot multivibrator U9A provides a RESET signal on the microcontroller.

The RESET signal automatically sets a logical "1" on "INTO" and the microcontroller starts a new cycle to determine the coordinates of the depressed key.

Other conventional electronic and logic components are shown in FIGS. 6A, 6B, 6C and 6D, be readily understandable to those skilled in the art. Typical operating values for the components shown in the circuit diagram of FIGS. 6A, 6B, 6C and 6D, are set forth in Table II below, which provides a listing of parts or components in which the first column indicates the quantity or number of components with particular characteristics used in the circuit diagram of FIGS. 6A, 6B, 6C and 6D, the second column provides the reference numeral by which such components are identified in FIGS. 6A, 6B, 6C and 6D, and the third column provides the specifications or electrical characteristics for the particular part or components. As will be recognized, an electronics engineer or technician will, by reference to the circuit diagram and Table II, be readily able to provide an operating circuit in accordance with the invention, as diagramed in FIG. 6.

TABLE II

PARTS SPECIFICATIONS FOR COMPONENTS OF HAND UNIT CIRCUIT

| Quantity of Component | Identifying Component Reference Numerals | Electrical Specifications |
|---|---|---|
| 1 | BT | +9V |
| 1 | C1 | 220pF |
| 4 | C2, C5, C6, C7 | 2.2uF |
| 2 | C3, C4 | 27pF |
| 16 | D1, D2, D3, D4, D5, D6, D7, D8, D9, D10, D11, D12, D13, D14, D15, D16 | BAW 56 |
| 1 | KB1 | KEY BOARD |
| 1 | Q1 | BSS 84 |
| 2 | Q2, Q3 | BSS 138 |
| 2 | R1, R2 | 10K |
| 4 | R3, R4, R5, R6 | 4.7K |
| 9 | R7, R8, R9, R10, R11, R12, R13, R14, R16 | 68K |
| 1 | R15 | 22K |
| 1 | R17 | 100K |
| 1 | R18 | 1K |
| 1 | S1 | SW SPST |
| 1 | U1 | 74HC132 |
| 1 | U2 | 74HC4520 |
| 1 | U3 | 74HC40103 |
| 2 | U4, U13 | 74HC74 |
| 1 | U5 | 74HC139B |
| 1 | U6 | 74HC126V |
| 1 | U7 | 74HC30B |
| 1 | U8 | 74HC151B |
| 1 | U9 | 74HC123B |
| 1 | U10 | 80C51B |
| 1 | U11 | 74HC573 |
| 1 | U12 | 27C256B |
| 1 | U14 | 74HC4066B |
| 1 | U15 | MAX 666 |
| 1 | Y1 | 3MHz |
| 1 | Y2 | 12MHz |

Although the preferred embodiment of the invention uses a small keyboard, other man/machine interface devices could readily be substituted without changing the basic nature of the invention. For example, the following input devices, not shown, would also provide acceptable input to the microprocessor: a miniature joystick with a control button, a trackball with control button or pressure-sense mechanism, a linear potentiometer with force-sensing capability and a series of coded buttons, each code corresponding to a location on the volume/frequency matrix.

The preferred embodiment of the invention uses a computer program, or software, to control a small microprocessor to determine the voice tones that will be provided by the artificial larynx of the invention. However, it will be recognized that hardware in the microprocessor itself could also be used to accomplish the same ends. In other words, the architecture, or operating system, of the microprocessor may be either all hardware or a combination of hardware plus software.

The waveforms which can be reproduced by the artificial larynx unit are stored in the memory of such unit and are reproduced in accordance with the keys which are depressed upon the control unit as to pitch and loudness. Each waveform, as known to those skilled in the art, will be represented by a separate number or representation with which the unit may be initially programmed either by the preferred software or in the basic hardware. The use of software to program the microprocessor is preferred, however, as it provides more flexibility and convenience. Such program arrangement is therefore described herein.

Two basic procedures for producing each waveform to be provided by the artificial larynx may be adopted.

In the one, a series of basic waveforms are stored in the main electronic memory of the microprocessor as data or in other peripheral or mass memory devices. Each wave form will be custom designed to provide not only the pitch and loudness as determined by the keys which are depressed, but also a basic repertoire of tonal quality, random noise in the higher frequency ranges, aspiration noise, random variation in the basic repetition rate of the fundamental tones, i.e. up to perhaps 0.5% random variation in the tone frequency, random absence of the tone pulse and the like. Normally, each of these will be determined by the tones stored in memory for the particular speaker. However, it will be understood that an alternative manner of operation is for the loudness-pitch signals provided by the unit under control of the keys pressed by the user, rather than having such additional elements of the usual speech tone already included in the particular tone stored in memory for that speaker, to instead have the basic tones stored in memory to be modified by the elements such as random noise, pulse omissions and the like to be superimposed upon the basic tones by further processing. In other words, rather than storing already modified tones with apparently random noise, minor variations in frequency, omitted pulses and the like for each speaker, the basic tones can be modified by further signals derived from memory or even under the control of the user. For example, a keyboard having additional keys for each of such additional qualities can be provided which the user can activate or not activate as he or she desires. Usually any such switches will be merely on-off-type switches, but other arrangements are also possible. Usually, however, it will be satisfactory and, in many cases, preferable, to merely provide as an initial tone signal keyed to each key on the keyboard, a particular tone which is already modified with the further variable explained above. Each tone in memory will, therefore, already be properly modified with random noise, random omissions of tonal pulses and the like and, such modified signal will consequently be initiated when the corresponding key is depressed. Alternatively, of course, a series of basic tones will be held in memory corresponding to each key and the modification of each tone to provide random noise, missing tonal pulses and the like will be accomplished by further instructions in the memory and program which causes each tone to be modified to provide the other elements of the invention prior to actual sending of the proper signal to the speaker for reproduction.

Figure 7:
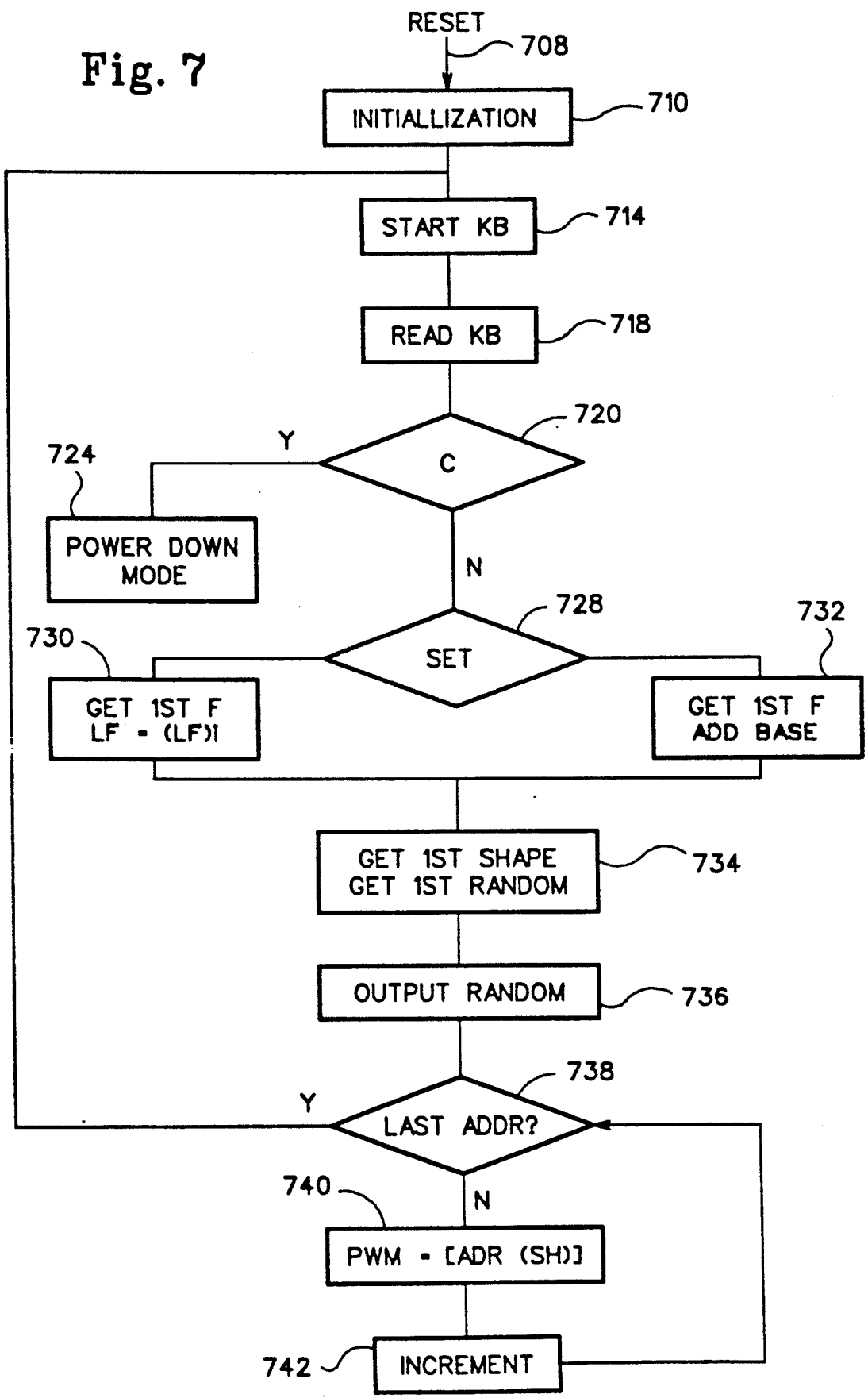
FIG. 7 is a flow chart of the computer program which controls the production of voice tones in the oral unit.

Referring to FIG. 7, the software code block diagram or flow sheet is illustrated for a preferred software program for use with the invention. The program begins with a RESET signal designated as 708. This results in progress to the next step, designated as 710, which effectively initializes the microprocessor. After initialization, a keyboard scan begins, as indicated by block 714. Once the keyboard is read, in accordance with block 718, the identity or location of the keys which are depressed is determined. Each frequency/volume value is stored in ROM.

If no buttons are found to be depressed, a differentiation function 720 comes into play and the microprocessor moves into the power down block mode, designated by block 724. From the power down mode, the system may be reactivated by a keyboard depression indication or sense which activates the RESET 708 indicated above. If a depressed button is sensed, the program determines if a "set" position exists, as per block 728. The "set" position allows the keyboard to shift from a first series of frequency/volume values, to a second series of frequency/volume values. This function is determined by the logic of blocks 730 and 732. Although the keyboard in a single "set" position can only access eight frequencies, for example, those eight notes can start on any first note and allow the user to choose the best frequency range for his speech. If a second button is depressed before the first one is released, the computer slides to the second tone using an interpolation program.

Once the frequency/volume location has been determined by functions 730 and 732, the program selects the initial value of the sequence in memory, block 734 and selects the initial value of the random delay variable. The random delay variable creates a pseudorandom frequency jitter simulating the random pulsing of the human voice, block 736. The delay is inserted before the pulse values are selected. After the delay is output and clocked, the program goes into a loop which steps through and outputs the amplitude values of the glottal pulse. This subroutine provides the PWM values for a single glottal pulse and then returns to check the keyboard for new input.

The waveform shape is stored in the read only memory which contains sufficient storage for more than 16 different frequencies and four independent loudness values. Because the waveform is stored in memory, the waveform for each frequency and loudness can be individually optimized to provide an accurate voice signal. The repetitive waveform may be analyzed as the sum of a series of harmonics of the fundamental frequency, each harmonic being a whole number multiple of the fundamental frequency and each having a well-defined amplitude. Preferable technique allows production of accurate waveforms with each harmonic defined within 2 db of the required amplitude to define a human-sounding voice excitation. Other approaches typically have used a single wave form for every frequency and amplitude setting without the ability to correct for any distortions in the system. Being able to accurately control and reproduce waveforms over a wide range of sound frequencies and volumes leads to a number of advantages over the prior art. Each tone and volume setting can be representative of an accurate voicing point. It is well known that as the voice is raised in volume at a fixed frequency not only does the sound get louder, but in addition, the waveform shape changes. The change in waveform change can be represented as a change in the relative amplitude of the harmonics which make up the wave form. The device of the invention allows one to reproduce the effect of changing harmonic content with changing volume which contributes to a realistic-sounding voice tone reproduction.

The output signal is transmitted from the hand or control unit to the oral unit by use of an antenna comprised of a ferrite rod which is wound with wire. The current passing through the wire creates a changing magnetic field which radiates energy to the mouth based detector.

The power supply 580 and 680 shown in FIGS. 5 and 6 uses or is based on the Maxim 666 integrated circuit which uses a nine volt battery for power and converts the battery potential to a stable 5 volt source for powering the logic, memory, and other microprocessor circuits.

In an alternate embodiment of the oral unit, the speaker may be mounted upon the palatal arch of the prosthesis 802 instead of inside or next to the cheek. Such arrangement has the advantage of eliminating some of the sound tubes, but requires typically a flatter speaker for user comfort. FIG. 8 is a partially broken away isometric view of such an alternative embodiment and shows a speaker 812 mounted in the palate section connected by wires 830 to a hybrid circuit 816 also mounted in the palate. A rubber membrane 822 protects the speaker from saliva and food. Also shown is a receptacle 850 for insertion of a charging plug and a receptacle cover 860 for protecting the receptacle from food or saliva during use. The cover is removed when the unit is removed from the mouth for charging. Rechargeable batteries 808 located, as in FIG. 1, in one side arch of the prosthesis are connected to receptacle 850 for recharging of the batteries 808. A screened opening 832 to a back pressure cavity, not shown, is positioned toward the front of the palate region of the prosthesis.

The unit of the invention may also be operated preferably in a "whisper mode" by providing a control, either in the form of an additional key on the hand-held unit, or on a key in an easily found location such as a corner key by which the sound made by forcefully expelling air through the larynx can be initiated and shaped by the normal speech apparatus without the use of a voice tone. This allows the laryngectomy patient to whisper, if desired, and closely mimics the usual whispered speech which comprises, in the normal person, speech produced without the usual voice tone produced by the larynx. Thus, the additional noises or sounds added to the artificial larynx tone, in accordance with the present invention, can be taken advantage of to provide a whisper made of speech for laryngectomees by merely eliminating the glottal vibration tone just as in actual whispering by not vibrating the laryngeal tissues.

As will be realized from the above discussion and description, the present invention not only provides an artificial larynx with a significantly more natural-sounding voice tone due to the additional refinements such as the inclusion of random noise, variations in frequency within certain limits, omitted pulses and the like, but also provides a particularly convenient and easily used and learned apparatus which can be readily used by a laryngectomy patient after only minimal training and practice as the result of providing a convenient handheld control readily controlled by one or more digits of the hand to provide a continuum of tones for forming into speech.

It will be realized also that while a hand control has been shown and described with a quadruple row of eight keys per row providing eight different tones and four possible loudnesses, that additional capacity can be added by the addition of more keys and operation in a somewhat more sophisticated mode by more than one hand digit such as, for example, the thumb plus a finger or the like.

It will also be realized that while the apparatus of the invention is usually provided with a limited capacity for memory of tones and related sounds and the like, that the unit can also be expanded as much as desired, consonant with maintaining a convenient size, with additional keys for special functions and combinations.

It should be understood, as indicated in general above, that although the present invention has been described at some length and in considerable detail and with some particularity with regard to several embodiments in connection with the accompanying figures and description, all such description and showing is to be considered as illustrative only and the invention is not intended to be narrowly interpreted in connection therewith or limited to any such particulars or embodiments, but should be interpreted broadly within the scope of the delineation of the invention set forth in the accompanying claims thereby to effectively encompass the intended scope of the invention.

I claim:

1. An artificial speech tone generation device for use by post-laryngectomy patients comprising:
    (a) a tone frequency generation means arranged and constructed to provide a substantially natural sounding artificial human voice tone within a human oral cavity for modulation by oral anatomy and movement,
    (b) a control means for manual operation by a user thereof including a hand activated control incorporating simultaneous on-off, pitch and volume control by a single control means over a predetermined continuum of control combinations combining pitch and volume,
    (c) said tone frequency generation means being arranged and constructed for accommodation intraorally and said control means being arranged and constructed for operation in a hand of the user whereby a post-laryngectomy patient may effectively control volume and pitch of an artificial human voice tone in a more natural sounding combination than otherwise, and
    (d) in which the control means for manual operation and the tone frequency generation means are arranged and configured for intercommunication via spacially transmitted information carrying waveforms.

2. An artificial tone generating device in accordance with claim 1, wherein the spacially transmitted information carrying waveforms constitute electromagnetic radiation.

3. An artificial tone generation device in accordance with claim 1 wherein the tone frequency generation means is arranged and constructed to provide at least one of a series of predetermined discontinuities and irregularities in tone generation including an particular slight random variations in repetition rate of fundamental tones.

4. An artificial tone generation device in accordance with claim 1 wherein the device is arranged and constructed to provide pulses of tonal frequencies with an occasional hiatus or diplophonic structure in such pulses of tonal frequencies, particularly in lower frequency ranges and volumes of such pulses to provide a more natural sounding speech tone.

5. An artificial tone generation device in accordance with claim 1 wherein the device is arranged and constructed to provide relatively minor amounts of random noise together with a voice tone.

6. An artificial speech tone generation device for use by a post-laryngectomy patient comprising:
    (a) an intraoral tone frequency generation means arranged and constructed to provide a substantially natural sounding voice tone with a post laryngectomy patient's oral cavity for modulation by mouth structures of said post laryngectomy patient,
    (b) a control means for manual operation by said post laryngectomy patient including a hand activated control incorporating on-off, pitch and volume control by a control means over a predetermined continuum of control combinations combining pitch and volume, (c) the hand activated control and intraoral tone frequency generation means being arranged and configured for intercommunication via spacially transmitted information carrying waveforms.

7. An artificial tone generation device in accordance with claim 6 wherein the tone frequency generation means is arranged and constructed to provide at least one of a series of predetermined discontinuities and irregularities in tone generation including in particular slight random variations in repetition rate of certain fundamental tones.

8. An artificial tone generation device in accordance with claim 6 wherein the device is arranged and constructed to provide an occasional hiatus or diplophonic structure in frequency pulses particularly in lower ranges of frequencies and volumes of such pulses to provide a more natural sounding speech tone.

9. An artificial tone generation device in accordance with claim 6 wherein the device is arranged and constructed to provide relatively minor amounts of random noise together with primary speech pulses creating an aspiration noise frequently associated with normal speech.

10. An artificial tone generation device in accordance with claim 6 wherein the device is arranged and constructed to provide random high frequency noise without primary speech tone pulses to create a speech pattern sometimes referred to as whispering.

11. An artificial tone generation device in accordance with claim 6 wherein communication between the control means and the tone frequency generation means is by electromagnetic radiation.

12. An artificial tone generation device in accordance with claim 6 wherein the control means incorporates a tone generating computer software program.

13. An artificial tone generation device in accordance with claim 12 wherein the computer software program is stored on a removable chip which is readily and conveniently interchanged with other chips incorporating tone generating programs to allow one basic tone generation device to create a multiplicity of different voice tones.

14. An artificial tone generation device in accordance with claim 6 wherein scanning between consecutive tones is smoothed by means of a tuned interpolation program controlled or run by a microcomputer.

15. An artificial speech tone generation device comprising:
(a) a tone frequency generation device arranged and constructed to provide a substantially natural sounding voice tone within a post laryngectomy patient's oral cavity for modulation by mouth structures of said post laryngectomy patient including a battery means, a loud speaker, an electronic circuit which can detect spacially transmitted signals and convert them to electrical signals for powering the loud speaker, and acoustic structures allowing wound to reach the oral cavity while protecting the loud speaker from saliva and bacteria,
(b) a control means for manual operation by the post laryngectomy patient including a hand activated control incorporating on-off means, plus pitch and volume control by a control means over a predetermined continuum of control combinations combining pitch and volume,
(c) said control means comprising a combined microcontroller and computer software program, and
(d) wherein an electromagnetic communication channel is used to transfer signals between the tone frequency generation device in the post laryngectomy patient's oral cavity and the control means for manual operation.

16. An artificial speech tone generation device in accordance with claim 15 wherein the frequency tone generation device is arranged and constructed to provide certain discontinuities in generated pulse tone of a random nature and to provide a small amount of high frequency random noise simulating aspiration noise.

17. An artificial tone generation device in accordance with claim 15 wherein the control means is configured with sufficient precision to output a waveform wherein harmonic amplitudes are individually defined to within 2 db of a predetermined value.

18. An artificial tone generation device in accordance with claim 15 wherein an acoustic path for a frequency tone incorporates a pressure relief vent which can pass air but will not pass bacteria or saliva.

19. An artificial tone generation device in accordance with claim 18 wherein the pressure relief valve is made from a halocarbon filter material.

20. An artificial tone generation device in accordance with claim 15 wherein the control means is arranged and constructed to provide discontinuities in generated tone of a random nature and a minor amount of high frequency random noise simulating aspiration noise and at least a portion of architecture of the control means includes a computer software program embodied upon a chip insertable as a unit into the control means.

21. An artificial larynx including an oral unit and a control unit:
(a) said oral unit comprising
  (i) prosthetic means for mounting an artificial larynx within a laryngectomy patient's oral cavity;
  (ii) a power source mounted in association with said prosthetic means;
  (iii) an electronic circuit for receiving and deciphering signals sent from a control unit;
  (iv) a power amplifier; and
  (v) a loud speaker;
(b) said control unit comprising:
  (i) a housing;
  (ii) a power source;
  (iii) an electronic circuit means; and
  (iv) a human interface device;
such units being arranged and constructed for generating, transmitting and receiving under control of a laryngectomy patient acoustic tonal pulse representations of a human glottal pulse to produce natural sounding speech, such control being arranged and constructed to activate and deactivate such pulse, to control a fundamental repetition rate of such pulse and to control both independently and jointly sound amplitude.

22. An artificial larynx in accordance with claim 21 wherein said control unit is additionally arranged and constructed to:
(c) control tonal quality of the tonal pulse representations.

23. An artificial larynx in accordance with claim 22 wherein said control unit is additionally arranged and constructed to:
(d) include aspiration noise in the tonal pulse representations.

24. An artificial larynx in accordance with claim 23 wherein said control unit is additionally arranged and constructed to:
  (e) include pseudorandom variation of the fundamental repetition rate of said tonal pulse representations.

25. An artificial larynx in accordance with claim 24 wherein said control unit is additionally arranged and constructed to:
  (f) include diplophonic structure in said tonal pulse representations.

26. An artificial larynx in accordance with claim 24 wherein said control unit is additionally arranged and constructed to:
  (g) include the ability to simulate whispering sound in place of said tonal pulse representations.

27. An artificial larynx in accordance with claim 21 wherein pitch and tone of said tonal representation are at least partially under direct control of the laryngectomy patient via the human interface device and other characteristics are substantially implemented by microprocessor means.

28. An artificial larynx in accordance with claim 27 wherein the microprocessor means includes software in its system architecture.